United States Patent [19]
Warzelhan et al.

[11] Patent Number: 5,889,135
[45] Date of Patent: Mar. 30, 1999

[54] BIODEGRADABLE POLYMERS, PROCESS FOR PRODUCING THEM AND THEIR USE IN PREPARING BIODEGRADABLE MOLDINGS

[75] Inventors: Volker Warzelhan, Weisenheim; Gunter Pipper, Bad Dürkheim; Ursula Seeliger, Ludwigshafen; Peter Bauer, Ludwigshafen; Udo Pagga, Ludwigshafen; Motonori Yamamoto, Mannheim, all of Germany

[73] Assignee: BASF Aktiengesellschaft, Ludwigshafen, Germany

[21] Appl. No.: 875,808

[22] PCT Filed: Mar. 5, 1996

[86] PCT No.: PCT/EP96/00457

§ 371 Date: Aug. 14, 1997

§ 102(e) Date: Aug. 14, 1997

[87] PCT Pub. No.: WO96/25446

PCT Pub. Date: Aug. 22, 1996

[30] Foreign Application Priority Data

Feb. 16, 1995 [DE] Germany .................. 195 05 185.8

[51] Int. Cl.⁶ .................................................. C08G 63/00
[52] U.S. Cl. ............................................................ 528/176
[58] Field of Search ............................................... 528/176

[56] References Cited

U.S. PATENT DOCUMENTS

| 3,803,259 | 4/1974 | Porchey et al. ............... 156/332 |
| 4,328,049 | 5/1982 | Richardson ................. 148/9 R |
| 4,328,059 | 5/1982 | Horlbeck et al. ............. 156/332 |

FOREIGN PATENT DOCUMENTS

| 21 942 | 1/1971 | European Pat. Off. . |
| 7 445 | 2/1980 | European Pat. Off. . |
| 13 471 | 7/1980 | European Pat. Off. . |
| 28 687 | 5/1981 | European Pat. Off. . |
| 372 846 | 6/1990 | European Pat. Off. . |
| 515 293 | 11/1992 | European Pat. Off. . |
| 534 295 | 3/1993 | European Pat. Off. . |
| 565 235 | 10/1993 | European Pat. Off. . |
| 818157 | 8/1959 | United Kingdom . |
| 1010916 | 11/1965 | United Kingdom . |
| 1115512 | 5/1968 | United Kingdom . |
| 1164331 | 9/1969 | United Kingdom . |
| 90/05161 | 5/1990 | WIPO . |
| 92/00441 | 1/1992 | WIPO . |
| 92/13019 | 8/1992 | WIPO . |

OTHER PUBLICATIONS

J. Applied Poly. Sci., vol. 32, 6191–6207 (1986).
Polymer. vol. 35, No. 18, 1994, Inhibiting effect of phosphorus compounds on model . . . , Fortunato et al.
Preparative Methods of Polymer Chem. Sorenson et al., Interscience Publishers, Inc., NY, 1961.
J. Biochem. vol., 59, No. 6, 1966, 537–545.
J. Appl. Pol. Sci. vol., 26, 1981 441–448.
Agr. Bio Chem., vol. 39, 1975, 1219–1223.
J. of App. Poly. Sci, vol. 24, 1701–1711 (1979).
Plant & Cell Physiol, 7, (1966) 93–103.
Nature Int. J. of Sci., vol. 270. Nov. 1977, 76–79.

*Primary Examiner*—Terressa Mosley
*Attorney, Agent, or Firm*—Keil & Weinkauf

[57] ABSTRACT

Biodegradable polyesters having a molecular weight ($M_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester at 25° C.), and a melting point of from 50 to 170° C., and having both hydroxyl and carboxyl end groups, the molar ratio of carboxyl end groups to hydroxyl end groups being greater than one, which is obtained by reacting a mixture consisting essentially of $a_1$) a mixture consisting essentially of
  from 45 to 80 mol % of adipic acid or ester-forming derivatives thereof, or mixtures thereof,
  from 20 to 55 mol % of terephthalic acid or ester-forming derivatives thereof, or mixtures thereof, and
  from 0 to 5 mol % of a sulfonate compound,
  where the sum of the individual mole percentages is 100 mol %, and $a_2$) a dihydroxy compound selected from the group consisting of $C_2$–$C_6$-alkanediols and $C_5$–$C_{10}$-cycloalkanediols, in the presence of from 0.01 to 5 mol %, per mol of component $a_1$), of a compound D having at least three groups capable of ester formation, the molar ratio of $a_1$) to $a_2$) being from 0.4:1 to 1.5:1, polymers and biodegradable thermoplastic molding compositions, processes for their preparation and their use for producing biodegradable moldings, adhesives, foams and blends with starch obtained from the polymers or molding compositions.

21 Claims, No Drawings

BIODEGRADABLE POLYMERS, PROCESS FOR PRODUCING THEM AND THEIR USE IN PREPARING BIODEGRADABLE MOLDINGS

The present invention relates to biodegradable polyesters P1 obtainable by reaction of a mixture consisting essentially of (a1) a mixture consisting essentially of from 35 to 95 mol % of adipic acid or ester-forming derivatives thereof or mixtures thereof, from 5 to 65 mol % of terephthalic acid or ester-forming derivatives thereof or mixtures thereof, and from 0 to 5 mol% of a sulfonate compound, the sum of the individual mole percentages being 100 mol %, and (a2) a dihydroxy compound selected from the group consisting of $C_2$–$C_6$-alkanediols and $C_5$–$C_{10}$-cycloalkanediols, the molar ratio of (a1) to (a2) being chosen within the range from 0.4:1 to 1.5:1, with the proviso that the polyesters P1 have a molecular weight ($M_n$) within the range from 5000 to 50,000 g/mol, a viscosity number within the range from 30 to 350 g/ml (measured in 50:50 w/w o-dichlorobenzene/phenol at a concentration of 0.5% by weight of polyester P1 at 25° C.) and a melting point within the range from 50° to 170° C. and with the further proviso that the polyesters P1 are prepared using from 0.01 to 5 mol %, based on the molar quantity used of component (a1), of a compound D having at least three groups capable of ester formation, and the further proviso that the polyesters P1 have both hydroxyl and carboxyl end groups, the molar ratio of carboxyl end groups to hydroxyl end groups being chosen to be greater than one.

The present invention further relates to polymers and biodegradable thermoplastic molding compositions as claimed in dependent claims, processes for their preparation, their use for producing biodegradable moldings, and adhesives, biodegradable moldings, foams and blends with starch obtainable from the polymers or molding compositions of the present invention.

Polymers which are biodegradable, ie. decompose under environmental influences in an appropriate and demonstrable time span, have been known for some time. This degradation usually takes place by hydrolysis and/or oxidation, but predominantly by the action of microorganisms such as bacteria, yeasts, fungi and algae. Y. Tokiwa and T. Suzuki (Nature, 270 (1977) 76–78) describe the enzymatic degradation of aliphatic polyesters, for example including polyesters based on succinic acid and aliphatic diols.

EP-A 565,235 describes aliphatic copolyesters containing [—NH—C(O)O—] groups (urethane units). The copolyesters of EP-A 565,235 are obtained by reacting a prepolyester, which is obtained by reacting essentially succinic acid and an aliphatic diol, with a diisocyanate, preferably hexamethylene diisocyanate. The reaction with the diisocyanate is necessary according to EP-A 565,235 because the polycondensation alone results only in polymers with molecular weights displaying unsatisfactory mechanical properties. A crucial disadvantage is the use of succinic acid or ester derivatives thereof to prepare the copolyesters because succinic acid and derivatives thereof are costly and are not available in adequate quantity on the market. In addition, the polyesters prepared using succinic acid as the only acid component are degraded only extremely slowly.

WO 92/13019 discloses copolyesters based on predominantly aromatic dicarboxylic acids and aliphatic diols, where at least 85 mol % of the polyester diol residue comprises a terephthalic acid residue. The hydrophilicity of the copolyester is increased, and the crystallinity is reduced, by modifications such as the incorporation of up to 2.5 mol % of metal salts of 5-sulfoisophthalic acid or short-chain ether diol segments such as diethylene glycol. This is said in WO 92/13019 to make the copolyesters biodegradable. However, the disadvantage of these copolyesters is that biodegradation by microorganisms has not been demonstrated, on the contrary only the behavior toward hydrolysis in boiling water or, in some cases, also with water at 60° C. has been carried out.

According to the statements of Y. Tokiwa and T. Suzuki (Nature, 270 (1977) 76–78 or J. of Appl. Polymer Science, 26 (1981) 441–448), it may be assumed that polyesters which are substantially composed of aromatic dicarboxylic acid units and aliphatic diols, such as PET (polyethylene terephthalate) and PBT (polybutylene terephthalate), are not enzymatically degradable.

This also applies to copolyesters which contain blocks composed of aromatic dicarboxylic acid units and aliphatic diols.

Witt et al. (handout for a poster at the International Workshop of the Royal Institute of Technology, Stockholm, Sweden, Apr. 21–23, 1994) describe biodegradable copolyesters based on 1,3-propanediol, terephthalic ester and adipic or sebacic acid. A disadvantage of these copolyesters is that moldings produced therefrom, especially sheets, have inadequate mechanical properties.

It is an object of the present invention to provide polymers which are degradable biologically, ie. by microorganisms, and which do not have these disadvantages. The intention was, in particular, that the polymers according to the invention be preparable from known and low-cost monomer units and be insoluble in water. It was furthermore the intention that it be possible to obtain products tailored for the desired uses according to the invention by specific modifications such as chain extension, incorporation of hydrophilic groups and groups having a branching action. The aim was moreover that the biodegradation by microorganisms is not to be achieved at the expense of the mechanical properties in order not to restrict the number of applications.

We have found that this object is achieved by the polymers and thermoplastic molding compositions defined at the outset.

We have also found processes for the preparation thereof, the use thereof for producing biodegradable moldings and adhesives, and biodegradable moldings, foams, blends with starch and adhesives obtainable from the polymers and molding compositions of the present invention.

The polyesters P1 of the present invention have a molecular weight ($M_n$) in the range from 5000 to 50,000, preferably from 6000 to 45,000, particularly preferably from 8000 to 35,000, g/mol, a viscosity number in the range from 30 to 350, preferably from 50 to 300, g/ml (measured in 50:50 w/w o-dichlorobenzene/phenol at a concentration of 0.5% by weight of polyester P1 at 25° C.) and a melting point in the range from 50° to 170°, preferably from 60° to 160° C., and have both hydroxyl and carboxyl end groups, the molar ratio of carboxyl end groups to hydroxyl end groups being chosen to be greater than one, preferably greater than two.

The polyesters P1 are obtained according to the invention by reaction of a mixture consisting essentially of (a1) a mixture consisting essentially of from 35 to 95, preferably from 45 to 80, mol % of adipic acid or ester-forming derivatives thereof, in particular the di-$C_1$–$C_6$-alkyl esters such as dimethyl, diethyl, dipropyl, dibutyl, dipentyl and dihexyl adipate, or mixtures thereof, preferably adipic acid and dimethyl adipate, or mixtures thereof, from 5 to 65, preferably 20 to 55, mol % of terephthalic acid or ester-forming derivatives thereof, in particular the di-$C_1$–$C_6$-alkyl esters such as dimethyl, diethyl, dipropyl, dibutyl, dipentyl or dihexyl terephthalate, or mixtures thereof, preferably terephthalic acid and dimethyl terephthalate, or mixtures thereof, and from 0 to 5, preferably from 0 to 3, particularly preferably from 0.1 to 2, mol % of a sulfonate compound, the sum of the individual mole percentages being 100 mol %, and (a2) a dihydroxy compound selected from the group consisting of $C_2$–$C_6$-alkanediols and $C_5$–$C_{10}$-cycloalkanediols, the molar ratio of (a1) to (a2) being chosen within the range from 0.4:1 to 1.5:1, preferably from 0.6:1 to 1.1:1.

The sulfonate compound which is normally employed is an alkali metal or alkaline earth metal salt of a dicarboxylic acid containing sulfonate groups, or the ester-forming derivatives thereof, preferably alkali metal salts of 5-sulfoisophthalic acid or mixtures thereof, particularly preferably the sodium salt.

The dihydroxy compounds (a2) employed according to the invention are selected from the group consisting of $C_2$–$C_6$-alkanediols and $C_5$–$C_{10}$-cycloalkanediols, such as ethylene glycol, 1,2- and 1,3-propanediol, 1,2- and 1,4-butanediol, 1,5-pentanediol or 1,6-hexanediol, in particular ethylene glycol, 1,3-propanediol and 1,4-butanediol, cyclopentanediol, 1,4-cyclohexanediol, 1,2-cyclohexanedimethanol, 1,4-cyclohexanedimethanol, and mixtures thereof.

Also used according to the invention are from 0.01 to 5, preferably from 0.05 to 4, mol %, based on component (a1), of at least one compound D having at least three groups capable of ester formation.

The compounds D preferably contain three to ten functional groups capable of forming ester linkages. Particularly preferred compounds D have three to six functional groups of this type in the molecule, in particular three to six hydroxyl groups and/or carboxyl groups. Examples which may be mentioned are:

tartaric acid, citric acid, malic acid;

trimethylolpropane, trimethylolethane;

pentaerythritol;

polyether triols;

glycerol;

trimesic acid;

trimellitic acid or anhydride;

pyromellitic acid or dianhydride and hydroxyisophthalic acid.

When compounds D which have a boiling point below 200° C. are used in the preparation of the polyesters P1, a proportion may distil out of the polycondensation mixture before the reaction. It is therefore preferred to add these compounds at an early stage of the process, such as the transesterification or esterification stage, in order to avoid this complication and in order to achieve the maximum possible uniformity of their distribution within the polycondensate.

In the case of compounds D which boil above 200° C., they can also be employed at a later stage of the process.

By adding the compound D it is possible, for example, to alter the melt viscosity in a desired manner, to increase the impact strength and to reduce the crystallinity of the polymers or molding compositions of the present invention.

The preparation of the biodegradable polyesters P1 is known in principle (Sorensen and Campbell, Preparative Methods of Polymer Chemistry, Interscience Publishers, Inc., New York, 1961, pages 111–127; Encycl. of Polym. Science and Eng., Vol. 12, 2nd Edition, John Wiley & Sons, 1988, pages 1–75; Kunststoff-Handbuch, Volume 3/1, Carl Hanser Verlag, Munich, 1992, pages 15–23 (Preparation of Polyesters); Wo 92/13019; EP-A 568, 593; EP-A 565, 235; EP-A 28, 687) so that details on this are superfluous.

Thus, for example, the reaction of dimethyl esters of component a1 with component a2 (transesterification) can be carried out at from 160° to 230° C. in the melt under atmospheric pressure, advantageously under an inert gas atmosphere.

In the preparation of the biodegradable polyester P1, it is advantageous to use a molar excess of component a2 relative to component a1, for example up to 2 ½ times, preferably up to 1.67 times.

The biodegradable polyester P1 is normally prepared with addition of suitable conventional catalysts such as metal compounds based on the following elements such as Ti, Ge, Zn, Fe, Mn, Co, Zr, V, Ir, La, Ce, Li, and Ca, preferably organometallic compounds based on these metals, such as salts of organic acids, alkoxides, acetylacetonates and the like, particularly preferably based on zinc, tin and titanium.

When dicarboxylic acids or anhydrides thereof are used as component (a1), esterification thereof with component (a2) can take place before, at the same time as or after the transesterification. In a preferred embodiment, the process described in DE-A 23 26 026 for preparing modified polyalkylene terephthalates is used.

After the reaction of components (a1) and (a2), the polycondensation is carried out as far as the desired molecular weight, as a rule under reduced pressure or in a stream of inert gas, for example of nitrogen, with further heating to from 180° to 260° C., taking into account the molar ratio of carboxyl end groups to hydroxyl end groups, which is chosen to be greater than 1, preferably greater than 2.

The required end group ratio can be set by an appropriate excess of component a1, by an appropriately long polycondensation time with simultaneous removal of the diol when there is an excess of component a2, or by adding an appropriate amount of polyfunctional carboxylic acids or derivatives thereof, preferably dicarboxylic anhydrides such as succinic anhydride, phthalic anhydride, pyromellitic anhydride or trimellitic anhydride, when polyester P1 has predominantly hydroxyl end groups owing to use of an excess of component a2.

In order to prevent unwanted degradation and/or side reactions, it is also possible at this stage of the process if required to add stabilizers. Examples of such stabilizers are the phosphorus compounds described in EP-A 13 461, U.S. Pat. No. 4,328,049 or in B. Fortunato et al., Polymer Vol. 35, No. 18, pages 4006–4010, 1994, Butterworth-Heinemann Ltd. These may also in some cases act as inactivators of the catalysts described above. Examples which may be mentioned are: organophosphites, phosphonous acid and phosphorous acid. Examples of compounds which act only as stabilizers are: trialkyl phosphites, triphenyl phosphite, trialkyl phosphates, triphenyl phosphate and tocopherol (vitamin E; obtainable as Uvinul® 2003AO (BASF) for example).

On use of the biodegradable copolymers of the present invention, for example in the packaging sector, eg. for foodstuffs, it is as a rule desirable to select the lowest possible content of catalyst employed and not to employ any toxic compounds. In contrast to other heavy metals such as lead, tin, antimony, cadmium, chromium, etc., titanium and zinc compounds are nontoxic as a rule (Sax Toxic Substance Data Book, Shizuo Fujiyama, Maruzen, K. K., 360 S. (cited in EP-A 565,235), see also Römpp Chemie Lexikon Vol. 6, Thieme Verlag, Stuttgart, New York, 9th Edition, 1992, pages 4626–4633 and 5136–5143). Examples which may be mentioned are: dibutoxydiacetoacetoxytitanium, tetrabutyl orthotitanate and zinc(II) acetate.

The ratio by weight of catalyst to biodegradable polyester P1 is normally in the range from 0.01:100 to 3:100, preferably from 0.05:100 to 2:100, it also being possible to employ smaller quantities, such as 0.0001:100, in the case of highly active titanium compounds.

The catalyst can be employed right at the start of the reaction, directly shortly before the removal of the excess diol or, if required, also distributed in a plurality of portions during the preparation of the biodegradable polyesters P1. It is also possible if required to employ different catalysts or mixtures thereof.

The biodegradable polyesters P2 of the present invention have a molecular weight ($M_n$) in the range from 5000 to 80,000, preferably from 6000 to 45,000, particularly preferably from 10,000 to 40,000, g/mol, a viscosity number in the range from 30 to 450, preferably from 50 to 400, g/ml (measured in 50:50 w/w o-dichlorobenzene/phenol at a concentration of 0.5% by weight of polyester P2 at 25° C.) and a melting point in the range from 50° to 235°, preferably from 60° to 235° C., and have both hydroxyl and carboxyl end groups, the molar ratio of carboxyl end groups to hydroxyl end groups being chosen to be greater than one, preferably greater than two.

The biodegradable polyesters P2 are obtained according to the invention by reaction of a mixture consisting essentially of (b1) a mixture consisting essentially of
  from 20 to 95, preferably from 25 to 80, particularly preferably from 30 to 70, mol % of adipic acid or ester-forming derivatives thereof or mixtures thereof,
  from 5 to 80, preferably from 20 to 75, particularly preferably from 30 to 70, mol % of terephthalic acid or ester-forming derivatives thereof or mixtures thereof, and
  from 0 to 5, preferably from 0 to 3, particularly preferably from 0.1 to 2, mol % of a sulfonate compound,
the sum of the individual mole percentages being 100 mol %,
(b2) dihydroxy compound (a2),
the molar ratio of (b1) to (b2) being chosen within the range from 0.4:1 to 1.5:1, preferably from 0.6:1 to 1.1:1,
  (b3) from 0.01 to 100, preferably from 0.1 to 80, % by weight, based on component (b1), of a hydroxycarboxylic acid 1, and
  (b4) from 0 to 5, preferably from 0 to 4, particularly preferably from 0.01 to 3.5, mol %, based on component (b1), of compound D,
the hydroxycarboxylic acid B1 being defined by the formula Ia or Ib

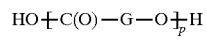  (Ia)

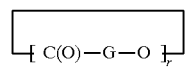  (Ib)

where p is an integer from 1 to 1500, preferably from 1 to 1000, r is 1, 2, 3 or 4, preferably 1 and 2, and G is a radical selected from the group consisting of phenylene, —($CH_2$)$_n$—, where n is an integer from 1, 2, 3, 4 or 5, preferably 1 and 5, —C(R)H— and —C(R)H$CH_2$, where R is methyl or ethyl.

The biodegradable polyesters P2 are expediently prepared in a similar way to the polyesters P1, it being possible to add the hydroxycarboxylic acid B1 either at the start of the reaction or after the esterification or transesterification stage.

In a preferred embodiment, the hydroxycarboxylic acid B1 employed is: glycolic acid, D-, L- or D,L-lactic acid, 6-hydroxyhexanoic acid, the cyclic derivatives thereof such as glycolide (1,4-dioxane-2,5-dione), D- or L-dilactide (3,6-dimethyl-1,4-dioxane-2,5-dione), p-hydroxybenzoic acid and oligomers and polymers thereof such as poly-3-hydroxybutyric acid, polyhydroxy-valeric acid, polylactide (obtainable as EcoPLA® from Cargill, for example) and a mixture of poly-3-hydroxybutyric acid and polyhydroxyvaleric acid (the latter is obtainable under the name Biopol® from Zeneca), particularly preferably the low molecular weight and cyclic derivatives thereof for the preparation of polyester P2.

The biodegradable polyesters Q1 of the present invention have a molecular weight($M_n$) in the range from 5000 to 100,000, preferably from 8000 to 80,000, a viscosity number in the range from 30 to 450, preferably from 50 to 400, g/ml (measured in 50:50% by weight o-dichlorobenzene/phenol at a concentration of 0.5% by weight of polyester Q1 at 25° C.) and a melting point in the range from 50° to 235°, preferably from 60° to 235° C., and have both hydroxyl and carboxyl end groups, the molar ratio of carboxyl end groups to hydroxyl end groups being chosen to be greater than one, preferably greater than 2.

The polyesters Q1 are obtained according to the invention by reaction of a mixture consisting essentially of
  (c1) polyester P1 and/or a polyester PWD,
  (c2) from 0.01 to 50, preferably from 0.1 to 40, % by weight, based on (c1), of hydroxycarboxylic acid B1, and
  (c3) from 0 to 5, preferably from 0 to 4, mol %, based on component (a1) from the preparation of P1 and/or PWD, of compound D.

The biodegradable polyester PWD is generally obtainable by reaction of essentially components (a1) and (a2), the molar ratio of (a1) to (a2) being chosen within the range from 0.4:1 to 1.5:1, preferably from 0.6:1 to 1.25:1, with the proviso that the polyesters PWD have a molecular weight ($M_n$) in the range from 5000 to 50,000, preferably from 6000 to 35,000, g/mol, a viscosity number in the range from 30 to 350, preferably from 50 to 300, g/ml (measured in 50:50 w/w o-dichlorobenzene/phenol at a concentration of 0.5% by weight of polyester PWD at 25° C.) and a melting point in the range from 50° to 170°, preferably from 60° to 160° C., and have both hydroxyl and carboxyl end groups, the molar ratio of carboxyl end groups to hydroxyl end groups being chosen to be greater than one, preferably greater than 2.

The reaction of the polyesters P1 and/or PWD with the hydroxycarboxylic acid B1, if required in the presence of compound D, preferably takes place in the melt at from 120° to 260° C. under an inert gas atmosphere, if desired also under reduced pressure. The procedure can be both batchwise and continuous, for example in stirred vessels or (reaction) extruders.

The reaction rate can, if required, be increased by adding conventional transesterification catalysts (see those described hereinbefore for the preparation of the polyesters P1).

A preferred embodiment relates to polyesters Q1 with block structures formed from components P1 and B1: when cyclic derivatives of B1 (compounds Ib) are used, it is possible in the reaction with the biodegradable polyester P1 to obtain, by a ring-opening polymerization initiated by the end groups of P1, in a conventional way polyesters Q1 with block structures (on the ring-opening polymerization, see Encycl. of Polym. Science and Eng. Vol. 12, 2nd Edition, John Wiley & Sons, 1988, pages 36–41). The reaction can, if required, be carried out with addition of conventional catalysts like the transesterification catalysts described hereinbefore, and tin octanoate is particularly preferred (see also Encycl. of Polym. Science and Eng. Vol. 12, 2nd Edition, John Wiley & Sons, 1988, pages 36–41).

When components B1 with higher molecular weights, for example with a p above 10 (ten) are used, it is possible to obtain, by reaction with the polyesters P1 in stirred vessels or extruders, the desired block structures by the choice of the reaction conditions such as temperature, holdup time, addition of transesterification catalysts like the abovementioned. Thus, J. of Appl. Polym. Sci., 32 (1986) 6191–6207 and Makromol. Chemie, 136 (1970) 311–313 disclose that in the reaction of polyesters in the melt it is possible to obtain from a blend by transesterification reactions initially block copolymers and then random copolymers.

The biodegradable polyesters Q2 of the present invention have a molecular weight ($M_n$) in the range from 6000 to 60,000, preferably from 8000 to 50,000, particularly preferably from 10,000 to 40,000, g/mol, a viscosity number in the range from 30 to 340, preferably from 50 to 300, g/ml (measured in 50:50% by weight o-dichlorobenzene/phenol at a concentration of 0.5% by weight of polyester Q2 at 25° C.) and a melting point in the range from 50° to 170° C., preferably from 60° to 160° C.

The polyesters Q2 are obtained according to the invention by reaction of a mixture consisting essentially of (d1) from 95 to 99.9, preferably from 96 to 99.8, particularly preferably from 97 to 99.65, % by weight of polyester P1 and/or polyester PWD as set forth in claim 3, (d2) from 0.1, to 5, preferably from 0.2 to 4, particularly preferably from 0.35 to 3, % by weight of a bisoxazoline C1 and (d3) from 0 to 5, preferably from 0 to 4, mol %, based on component (a1) from the preparation of P1 and/or PWD, of compound D.

Bisoxazolines C1 which can be used are, according to observations hitherto, all conventional bisoxazolines. Examples of appropriate bisoxazolines are described in DE-A 39 15 874 (commercially available under the name Loxamid e). Other bisoxazolines are described in WO 94/03523 (PCT/EP 93/01986).

Particularly preferred bisoxazolines C1 are bisoxazolines of the general formula II

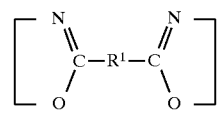

The bisoxazolines C1 of the general formula II (component d2) are generally obtainable via the process of Angew. Chem. Int. Edit., 11 (1972) 287–288. Particularly preferred bisoxazolines are those where $R^1$ is a single bond, a $(CH_2)_q$ alkylene group with q=2, 3 or 4, such as methylene, ethane-1,2-diyl, propane-1,3-diyl, propane-1,2-diyl, butane-1,4-diyl or a phenylene group. Particularly preferred bisoxazolines which may be mentioned are 2,2'-bis(2-oxazoline), bis(2-oxazolinyl)methane, 1,2-bis(2-oxazolinyl)ethane, 1,3-bis(2-oxazolinyl)propane, 1,4-bis(2-oxazolinyl)butane, 1,4-bis(2-oxazolinyl)benzene, 1,2-bis(2-oxazolinyl)benzene and 1,3-bis(2-oxazolinyl)benzene.

The polyesters P1 and/or PWD are reacted with the bisoxazoline C1 preferably in the melt (see also: J. Appl. Polym. Science, 33 (1987) 3069–3079), it being necessary to take care that, if possible, no side reactions which may lead to crosslinking or gel formation occur. In a particular embodiment, the reaction is normally carried out at from 120° to 260° C., preferably from 130° to 240° C., particularly preferably from 140° to 220° C., with the addition of the bisoxazoline advantageously taking place in a plurality of portions or continuously.

If required, it is also possible to carry out the reaction of the polyesters P1 and/or PWD with the bisoxazoline C1 in the presence of conventional inert solvents such as toluene, methyl ethyl ketone or dimethylformamide (DMF) or mixtures thereof, in which case the reaction is as a rule carried out from 80° to 200°, preferably from 90° to 150° C.

The reaction with the bisoxazoline C1 can be carried out batchwise or continuously, for example in stirred vessels, reaction extruders or through mixing heads.

Although the theoretical optimum for the reaction of P1 and/or PWD with bisoxazolines C1 is a molar ratio of the oxazoline functionality to P1 (or PWD) carboxyl end group (polyesters P1 and/or PWD with predominantly carboxyl end groups are particularly preferred) of 1:1, the reaction can also be carried out with molar ratios of from 1:3 to 1.5:1 without technical problems. With the molar ratios of >1:1, preferably >2:1, according to the invention it is possible, if required, to add, during the reaction or else after the reaction, a dicarboxylic acid, preferably selected from the group consisting of adipic acid, succinic acid, terephthalic acid and isophthalic acid.

The biodegradable polymers T1 of the present invention have a molecular weight ($M_n$) in the range from 10,000 to 100,000, preferably from 11,000 to 80,000, preferably from 11,000 to 50,000, g/mol, a viscosity number in the range from 30 to 450, preferably from 50 to 400, g/ml (measured in 50:50 w/w o-dichlorobenzene/phenol at a concentration of 0.5% by weight of polymer T1 at 25° C.) and a melting point in the range from 50° to 235°, preferably from 60° to 235° C.

The biodegradable polymers T1 are obtained according to the invention by reaction of a polyester Q1 as set forth in claim 3 with (e1) from 0.1 to 5, preferably from 0.2 to 4, particularly preferably from 0.3 to 2.5, % by weight, based on the polyester Q1, of bisoxazoline C1 and with (e2) from 0 to 5, preferably from 0 to 4, mol %, based on component (a1) from the preparation of P1 and/or PWD and polyester Q1, of compound D.

This normally results in a chain extension, with the resulting polymer chains preferably having a block structure.

The reaction is, as a rule, carried out in a similar way to the preparation of the polyesters Q2.

The biodegradable polymers T2 of the present invention have a molecular weight ($M_n$) in the range from 10,000 to 100,000, preferably from 11,000 to 80,000, particularly preferably from 11,000 to 50,000, g/mol, a viscosity number in the range from 30 to 450, preferably from 50 to 400, g/ml (measured in 50:50 w/w o-dichlorobenzene/phenol at a concentration of 0.5% by weight of polymer T2 at 25° C.) and a melting point in the range from 50° to 235°, preferably from 60° to 235° C.

The biodegradable polymers T2 are obtained according to the invention by reaction of the polyester Q2 with (f1) from 0.01 to 50, preferably from 0.1 to 40, % by weight, based on the polyester Q2, of the hydroxycarboxylic acid B1 and with (f2) from 0 to 5, preferably from 0 to 4, mol %, based on component (a1) from the preparation of PI and/or PWD and of the polyester Q2, of compound D, the process expediently being similar to the reaction of polyester P1 with hydroxycarboxylic acid B1 to give polyester Q1.

The biodegradable polymers T3 of the present invention have a molecular weight ($M_n$) in the range from 10,000 to 100,000, preferably from 11,000 to 80,000, g/mol, a viscosity number in the range from 30 to 450, preferably from 50 to 400, g/ml (measured in 50:50 w/w o-dichlorobenzene/ phenol at a concentration of 0.5% by weight of polymer T3 at 25° C.) and a melting point in the range from 50° to 235°, preferably from 60° to 235° C.

The biodegradable polymers T3 are obtained according to the invention by reaction of (g1) polyester P2, or (g2) a mixture consisting essentially of polyester P1 and from 0.01 to 50, preferably from 0.1 to 40, % by weight, based on the polyester P1, of hydroxycarboxylic acid B1, or (g3) a mixture consisting essentially of polyesters P1 which have mutually different compositions, with from 0.1 to 5, preferably from 0.2 to 4, particularly preferably from 0.3 to 2.5, % by weight, based on the amount of polyesters used, of bisoxazoline C1 and with from 0 to 5, preferably from 0 to 4, mol %, based on the respective molar quantities of component (a1) used for preparing the polyesters (g1) to (g3) used, of compound D, the reactions expediently being carried out in a similar way to the preparation of the polyesters Q2 from the polyesters P1 and/or PWD and the bisoxazolines C1.

In a preferred embodiment, polyesters P2 whose repeating units are randomly distributed in the molecule are employed.

However, it is also possible to employ polyesters P2 whose polymer chains have block structures. Polyesters P2 of this type can generally be obtained by appropriate choice, in particular of the molecular weight, of the hydroxycarboxylic acid B1. Thus, according to observations to date there is generally only incomplete transesterification when a high molecular weight hydroxycarboxylic acid B1 is used, in particular with a p above 10, for example also in the presence of the inactivators described above (see J. of Appl. Polym. Sci. 32 (1986) 6191–6207 and Makromol. Chemie 136 (1970) 311–313). If required, the reaction can also be carried out in solution using the solvents mentioned for the preparation of the polymers T1 from the polyesters Q1 and the bisoxazolines C1.

The biodegradable thermoplastic molding compositions T4 are obtained according to the invention by conventional mixing, preferably with the addition of conventional additives such as stabilizers, processing aids, fillers etc. (see J. of Appl. Polym. Sci., 32 (1986) 6191–6207; WO 92/0441; EP 515,203; Kunststoff-Handbuch, Vol. 3/1, Carl Hanser Verlag, Munich, 1992, pages 24–28), of (h1) from 99.5 to 0.5% by weight of polyester P1 as set forth in claim 1 or polyester Q2 as set forth in claim 4 or polyester PWD as set forth in claim 3 with (h2) from 0.5 to 99.5% by weight of hydroxycarboxylic acid B1.

In a preferred embodiment, high molecular weight hydroxycarboxylic acids B1 such as polycaprolactone or polylactide or polyglycolide or polyhydroxyalkanoates such as poly-3-hydroxybutyric acid with a molecular weight ($M_n$) in the range from 10,000 to 150,000, preferably from 10,000 to 100,000, g/mol, or a mixture of poly-3-hydroxybutyric acid and polyhydroxyvaleric acid are employed.

Wo 92/0441 and EP-A 515,203 disclose that high molecular weight polylactide without added plasticizers is too brittle for most applications. It is possible in a preferred embodiment to prepare a blend, starting from 0.5–20, preferably 0.5–10, % by weight of polyester P1 as set forth in claim 1 or polyester Q2 as set forth in claim 4 or polyester PWD as set forth in claim 3 and 99.5–80, preferably 99.5–90, % by weight of polylactide, which displays a distinct improvement in the mechanical properties, for example an increase in the impact strength, compared with pure polylactide.

Another preferred embodiment relates to a blend obtainable by mixing from 99.5 to 40, preferably from 99.5 to 60, % by weight of polyester P1 as set forth in claim 1 or polyester Q2 as set forth in claim 4 or polyester PWD as set forth in claim 3 and from 0.5 to 60, preferably from 0.5 to 40, % by weight of a high molecular weight hydroxycarboxylic acid B1, particularly preferably polylactide, polyglycolide, poly-3-hydroxybutyric acid and polycaprolactone. Blends of this type are completely biodegradable and, according to observations to date, have very good mechanical properties.

According to observations to date, the thermoplastic molding compositions T4 according to the invention are preferably obtained by observing short mixing times, for example when carrying out the mixing in an extruder. It is also possible to obtain molding compositions which have predominantly blend structures by choice of the mixing parameters, in particular the mixing time and, if required, the use of inactivators, ie. it is possible to control the mixing process so that transesterification reactions can also take place at least partly.

In another preferred embodiment, it is possible to replace 0–50, preferably 0–30, mol % of the adipic acid or the ester-forming derivatives thereof or the mixtures thereof by at least one other aliphatic $C_4$–$C_{10}$- or cycloaliphatic $C_5$–$C_{10}$-dicarboxylic acid or dimer fatty acid such as succinic acid, glutaric acid, pimelic acid, suberic acid, azelaic acid or sebacic acid or an ester derivative such as the di-$C_1$–$C_6$-alkyl esters thereof or the anhydrides thereof such as succinic anhydride, or mixtures thereof, preferably succinic acid, succinic anhydride, sebacic acid, dimer fatty acid and di-$C_1$–$C_6$-alkyl esters such as dimethyl, diethyl, di-n-propyl, diisobutyl, di-n-pentyl, dineopentyl, di-n-hexyl esters thereof, especially dimethyl succinate.

A particularly preferred embodiment relates to the use as component (a1) of the mixture, described in EP-A 7445, of succinic acid, adipic acid and glutaric acid and the $C_1$–C6-alkyl esters thereof, especially the dimethyl ester and diisobutyl ester.

In another preferred embodiment it is possible to replace 0–50, preferably 0–40, mol % of the terephthalic acid or the ester-forming derivatives thereof, or the mixtures thereof, by at least one other aromatic dicarboxylic acid such as isophthalic acid, phthalic acid or 2,6-naphthalenedicarboxylic acid, preferably isophthalic acid, or an ester derivative such as a di-$C_1$-$C_6$-alkyl ester, in particular the dimethyl ester, or mixtures thereof.

It should be noted in general that the various polymers according to the invention can be worked up in a conventional way by isolating the polymers or, in particular if it is wished to react the polyesters P1, P2, Q1 and Q2 further, by not isolating the polymers but immediately processing them further.

The polymers according to the invention can be applied to coating substrates by rolling, spreading, spraying or pouring. Preferred coating substrates are those which are compostable or rot such as moldings of paper, cellulose or starch.

The polymers according to the invention can also be used to produce moldings which are compostable. Moldings which may be mentioned by way of example are: disposable articles such as crockery, cutlery, refuse sacks, sheets for agriculture to advance harvesting, packaging sheets and vessels for growing plants.

It is furthermore possible to spin the polymers according to the invention into threads in a conventional way. The threads can, if required, be stretched, stretch-twisted, stretch-wound, stretch-warped, stretch-sized and stretch-texturized by conventional methods. The stretching to flat yarn can moreover take place in the same working step (fully drawn yarn or fully oriented yarn) or in a separate step. The stretch warping, stretch sizing and stretch texturizing are generally carried out in a working step separate from the spinning. The threads can be further processed to fibers in a conventional way. Sheet-like structures can then be obtained from the fibers by weaving or knitting.

The moldings, coating compositions and threads etc. described above can, if required, also contain fillers which can be incorporated during the polymerization process at any stage or subsequently, for example in a melt of the polymers according to the invention.

It is possible to add from 0 to 80% by weight of fillers, based on the polymers according to the invention. Examples of suitable fillers are carbon black, starch, lignin powder, cellulose fibers, natural fibers such as sisal and hemp, iron oxides, clay minerals, ores, calcium carbonate, calcium sulfate, barium sulfate and titanium dioxide. The fillers can in some cases also contain stabilizers such as tocopherol (vitamin E), organic phosphorus compounds, mono-, di- and polyphenols, hydroquinones, diarylamines, thioethers, UV stabilizers, nucleating agents such as talc, and lubricants and mold release agents based on hydrocarbons, fatty alcohols, higher carboxylic acids, metal salts of higher carboxylic acids such as calcium and zinc stearate, and montan waxes. Such stabilizers etc. are described in detail in Kunststoff-Handbuch, Vol. 3/1, Carl Hanser Verlag, Munich, 1992, pages 24–28.

The polymers according to the invention can additionally be colored in any desired way by adding organic or inorganic dyes. The dyes can also in the widest sense be regarded as fillers.

A particular application of the polymers according to the invention relates to the use as compostable sheet or a compostable coating as outer layer of diapers. The outer layer of the diapers effectively prevents penetration by liquids which are absorbed inside the diaper by the fluff and superabsorbers, preferably by biodegradable superabsorbers, for example based on crosslinked polyacrylic acid or crosslinked polyacrylamide. It is possible to use a web of a cellulose material as inner layer of the diaper. The outer layer of the described diapers is biodegradable and thus compostable. It disintegrates on composting so that the entire diaper rots, whereas diapers provided with an outer layer of, for example, polyethylene cannot be composted without previous reduction in size or elaborate removal of the polyethylene sheet.

Another preferred use of the polymers and molding compositions according to the invention relates to the production of adhesives in a conventional way (see, for example, Encycl. of Polym. Sci. and Eng. Vol.1, "Adhesive Compositions", pages 547–577). The polymers and molding compositions according to the invention can also be processed as disclosed in EP-A 21042 using suitable tackifying thermoplastic resins, preferably natural resins, by the methods described therein. The polymers and molding compositions according to the invention can also be further processed as disclosed in DE-A 4, 234, 305 to solvent-free adhesive systems such as hot melt sheets.

Another preferred application relates to the production of completely degradable blends with starch mixtures (preferably with thermoplastic starch as described in Wo 90/05161) in a similar process to that described in DE-A 42 37 535. The polymers and thermoplastic molding compositions according to the invention can, according to observations to date, because of their hydrophobic nature, their mechanical properties, their complete biodegradability, their good compatibility with thermoplastic starch and not least because of their favorable raw material basis, advantageously be employed as synthetic blend component.

Further applications relate, for example, to the use of the polymers according to the invention in agricultural mulch, packaging materials for seeds and nutrients, substrate in adhesive sheets, baby pants, pouches, bed sheets, bottles, boxes, dust bags, labels, cushion coverings, protective clothing, hygiene articles, handkerchiefs, toys and wipes.

Another use of the polymers and molding compositions according to the invention relates to the production of foams, generally by conventional methods (see EP-A 372, 846; Handbook of Polymeric foams and Foam Technology, Hanser Publisher, Munich, 1991, pages 375–408). This normally entails the polymer or molding composition according to the invention being initially melted, if required with the addition of up to 5% by weight of compound D, preferably pyromellitic dianhydride and trimellitic anhydride, then a blowing agent being added and the resulting mixture being exposed to a reduced pressure by extrusion, resulting in foaming.

The advantages of the polymers according to the invention over known biodegradable polymers are a favorable raw material basis with readily available starting materials such as adipic acid; terephthalic acid and conventional diols, interesting mechanical properties due to the combination of "hard" (owing to the aromatic dicarboxylic acids such as terephthalic acid) and "soft" (owing to the aliphatic dicarboxylic acids such as adipic acid) segments in the polymer chain and the variation in uses due to simple modifications, a satisfactory degradation by microorganisms, especially in compost and soil, and a certain resistance to microorganisms in aqueous systems at room temperature, which is particularly advantageous for many applications. The random incorporation of the aromatic dicarboxylic acids of components (a1) in various polymers makes the biological attack possible and thus achieves the desired biodegradability.

A particular advantage of the polymers according to the invention is that it is possible by tailoring the formulations to optimize both the biodegradation and the mechanical properties for the particular application.

It is furthermore possible, depending on the preparation process, advantageously to obtain polymers with predominantly random distribution of monomer units, polymers with predominantly block structures and polymers with predominantly blend structure or blends.

EXAMPLES

Enzyme assay

The polymers were cooled with liquid nitrogen or dry ice and finely ground in a mill (the rate of enzymatic degradation increases with the surface area of the ground material). For the actual enzyme assay, 30 mg of finely ground polymer powder and 2 ml of a 20 mM aqueous $K_2HPO_4/KH_2PO_4$ buffer solution (pH: 7.0) were placed in an Eppendorf tube (2 ml) and equilibrated at 37° C. in a rotary mixer for 3 h. Then 100 units of lipase from either Rhizopus arrhizus, Rhizopus delemar or Pseudomonas pl. were added and incubation was carried out at 37° C. in the rotary mixer (250 rpm) for 16 h. The reaction mixture was then filtered through a Millipores membrane (0.45 $\mu$m) and the DOC (dissolved organic carbon) of the filtrate was measured. A DOC measurement was carried out in a similar way once with only buffer and enzyme (as enzyme control) and once with only buffer and sample (as blank).

The $\Delta$DOC values found (DOC(sample+enzyme)-DOC (enzyme control)-DOC(blank)) can be regarded as a measure of the enzymatic degradability of the samples. They are shown in each case comparing with a measurement on powder from polycaprolactone® Tone P 787 (Union Carbide). In the assessment, it should be noted that these are not absolutely quantifiable data. The connection between the surface area of the ground material and the speed of enzymatic degradation has been pointed out above. It is furthermore possible for the enzyme activities to vary.

The molecular weights were measured by gel permeation chromatography (GPC):

stationary phase: 5 MIXED B polystyrene gel columns (7.5×300 mm, PL gel 10 $\mu$) from Polymer Laboratories; equilibration: 35° C.;

mobile phase: tetrahydrofuran (flow rate: 1.2 ml/min)

calibration: molecular weight 500–10,000,000 g/mol with PS calibration kit from Polymer Laboratories.

In the oligomer region ethylbenzene/1,3-diphenylbutane/1,3,5-triphenylhexane/1,3,5,7-tetraphenyloctane/1,3,5,7,9-pentaphenyldecane detection: RI (refractive index) Waters 410 UV (at 254 nm) Spectra Physica 100

The following methods were used to determine the hydroxyl number (OH number) and acid number (AN):

(a) Determination of the Apparent Hydroxyl Number 10 ml of toluene and 9.8 ml of acetylating reagent (see below) were added to about 1 to 2 g of accurately weighed test substance and the mixture was heated at 95° C. with stirring for 1 h. Then 5 ml of distilled water were added. After cooling to room temperature, 50 ml of tetrahydrofuran (THF) were added and potentiographic titration was carried out with ethanolic KOH standard solution to the turning point.

The test was repeated without test substance (blank sample).

The apparent OH number was then determined using the following formula:

apparent OH number c.t. 56.1.(V2–V1)/m (in mg KOH/g)

where c=amount of substance concentration of the ethanolic

KOH standard solution in mol/l, t=titer of the ethanolic KOH standard solution m=weight of test substance in mg V1=ml of standard solution used with test substance V2=ml of standard solution used without test substance.

Reagents used:

ethanolic KOH standard solution, c=0.5 mol/l, titer 0.9933 (Merck, Cat. No. 1.09114)

acetic anhydride analytical grade (Merck, Cat. No. 42)

pyridine analytical grade (Riedel de Haen, Cat. No. 33638)

acetic acid analytical grade (Merck, Cat. No. 1.00063)

acetylating reagent: 810 ml of pyridine, 100 ml of acetic anhydride and 9 ml of acetic acid water, deionized THF and toluene b) Determination of the Acid Number (AN)

About 1 to 1.5 g of test substance were weighed accurately, mixed with 10 ml of toluene and 10 ml of pyridine and then heated to 95° C. After dissolving, the solution was cooled to room temperature, 5 ml of water and 50 ml of THF were added and titration was carried out with 0.1N ethanolic KOH standard solution.

The determination was repeated without test substance (blank sample)

The acid number was then determined using the following formula:

$$AN = c \cdot t \cdot 56.1 \cdot (V1-V2)/m \text{ (in mg KOH/g)}$$

where c=amount of substance concentration of the ethanolic

KOH standard solution in mol/l t=titer of the ethanolic KOH standard solution m=weight of test substance in mg V1=ml of standard solution used with test substance V2 =ml of standard solution used without test substance.

Reagents used:

ethanolic KOH standard solution, c=0.1 mol/l, titer= 0.9913 (Merck, Cat. No. 9115)

pyridine analytical grade (Riedel de Haen, Cat. No. 33638)

Water, deionized

THF and toluene (c) Determination of the OH Number

The OH number is found from the sum of the apparent OH number and the AN

OH number=apparent OH number+AN

Abbreviations used:

DOC: dissolved organic carbon

DMT: dimethyl terephthalate

PCL: polycaprolactone® Tone P 787 (Union Carbide)

PMDA: pyromellitic dianhydride

AN: acid number

TBOT: tetrabutyl orthotitanate

VN: viscosity number (measured in o-dichlorobenzene/phenol (50/50 ratio by weight) at a concentration of 0.5% by weight polymer at 25° C.)

$T_m$: "melting temperature"=temperature at which a maximum endothermic heat flux occurs (extreme of the DSC plots)

$T_g$: glass transition temperature (midpoint of the DSC plots)

The DSC measurements were carried out with a DuPont 912+Thermal Analyzer 990 DSC apparatus. The temperature and enthalpy calibration took place in the usual way. The sample weight was typically 13 mg. The heating and cooling rates were 20 K/min except where noted otherwise. The samples were measured under the following conditions: 1. heating run on samples as supplied, 2. rapid cooling from the melt, 3. heating run on samples cooled from the melt (samples from 2). The second DSC runs in each case made it possible to compare the various samples after a uniform thermal history.

EXAMPLE 1

Preparation of a Polyester P1

(a) 4672 kg of 1,4-butanediol, 7000 kg of adipic acid and 50 g of tin dioctoate were reacted under a nitrogen atmosphere at 230 to 240° C. After most of the water formed in the reaction had been removed by distillation, 10 g of TBOT were added to the reaction mixture. After the acid number had fallen below 1, excess 1,4-butanediol was distilled out under reduced pressure until the OH number reached 56.

(b) 1.81 kg of the polyester from Example 1a, 1.17 kg of DMT, 1.7 kg of 1,4-butanediol and 4.7 g of TBOT plus 6.6 g of PMDA were placed in a three-neck flask and heated under a nitrogen atmosphere to 180° C. while stirring slowly. During this, the methanol formed in the transesterification was distilled out. The mixture was heated to 230° C. over the course of 2 h while increasing the stirring speed and, after a further hour, 2 g of 50% by weight aqueous phosphorous acid were added. The pressure was reduced to 5 mbar over the course of 1 h and was kept at <2 mbar and 240° C. for 2.5 h, during which the excess 1,4-butanediol distilled out.

OH number: 1 mg KOH/g
AN: 8.8 mg KOH/g
VN: 98.2 g/ml
$T_m$: 93° C. (DSC, as supplied), $T_g$: −39° C.

EXAMPLE 2

Preparation of a Polyester Q2

26.25 g of the bisoxazoline bis(2-ricinoleyl-2-oxazolinyl)-tetramethylxylene diurethane (Loxamid® VEP 8523 supplied by Henkel, a bisoxazoline from ricinoleyloxazoline and 4,4'-diphenylmethane diisocyanate, which can be prepared in accordance with DE-A 39 15 874) were added dropwise over the course of 30 min to 300 g of the copolyester from Example 1a while stirring at 200° C. under a nitrogen atmosphere, during which the melt viscosity increased and the product became brownish.
OH number: 2 mg KOH/g
AN: 1.9 mg KOH/g
$T_m$: 97° C., $T_g$: −34° C. (DSC, rapidly cooled from 190° C.)
Enzyme assay with Rhizopus arrhizus: ADOC: 357 mg/l; for comparison with PCL: ΔDOC: 2588 mg/l.

EXAMPLE 3

Preparation of another Polyester Q2

6.9 g of the bisoxazoline 1,4-bis(2-oxazolinyl)butane were added dropwise over the course of 10 min to 300 g of the copolyester from Example 1a while stirring at 200° C. under a nitrogen atmosphere, during which the melt viscosity increased and the product became brownish.

OH number: 3 mg KOH/g
AN: 2 mg KOH/g
$T_m$: 99° C., $T_g$: −31° C. (DSC, as supplied)
Enzyme assay with Rhizopus arrhizus: ΔDOC: 421 mg/l; for comparison with PCL: ΔDOC: 2588 mg/l.

We claim:

1. A biodegradable polyester P1 having
   a molecular weight ($M_n$) of from 5000 to 50,000 g/mol (measured by gel permeation chromatography),
   a viscosity number of from 30 to 350 g/ml (measured in 50:50 by weight of o-dichlorobenzene/phenol at a concentration of 0.5% by weight of polyester P1 at 25° C.), and
   a melting point of from 50° to 170° C.,
   and having both hydroxyl and carboxyl end groups, the molar ratio of carboxyl end groups to hydroxyl end groups being greater than one,
   which is obtained by reacting a mixture consisting essentially of
   $a_1$) a mixture consisting essentially of
      from 45 to 80 mol % of adipic acid or ester-forming derivatives thereof, or mixtures thereof,
      from 20 to 55 mol % of terephthalic acid or ester-forming derivatives thereof, or mixtures thereof, and
      from 0 to 5 mol % of a sulfonate compound,
      where the sum of the individual mol % percentages is 100 mol %, and
   $a_2$) a dihydroxy compound selected from the group consisting of
      $C_2$–$C_6$-alkanediols and $C_5$–$C_{10}$-cycloalkanediols, in the presence of from 0.01 to 5 mol %, per mol of component $a_1$), of a compound D having at least three groups capable of ester formation, the molar ratio of $a_1$) to $a_2$) being from 0.4:1 to 1.5:1.

2. A biodegradable polyester P2 having
   a molecular weight ($M_n$) of from 5000 to 80,000 g/mol (measured by gel permeation chromatography),
   a viscosity number of from 30 to 450 g/ml (measured in 50:50 by weight of o-dichlorobenzene/phenol at a concentration of 0.5% by weight of polyester P2 at 25° C.), and
   a melting point of from 50 to 235° C.,
   and having both hydroxyl and carboxyl end groups, the molar ratio of carboxyl end groups to hydroxyl end groups being greater than one,
   which is obtained by reacting a mixture consisting essentially of
   $b_1$) a mixture consisting essentially of
      from 25 to 80 mol % of adipic acid or ester-forming derivatives thereof, or mixtures thereof,
      from 20 to 75 mol % of terephthalic acid or ester-forming derivatives thereof, or mixtures thereof, and
      from 0 to 5 mol % of a sulfonate compound,
      where the sum of the individual mol % percentages is 100 mol %,
   $b_2$) a dihydroxy compound $a_2$) selected from the group consisting of $C_2$–$C_6$-alkanediols and $C_5$–$C_{10}$-cycloalkanediols,
   $b_3$) from 0.01 to 100% by weight, per weight of component $b_1$), of a hydroxycarboxylic acid B1 being defined by the formula I$a$ or I$b$

-continued

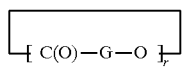  (Ib)

where p is an integer from 1 to 1500, r is an integer from 1 to 4, and G is a radical selected from the group consisting of phenylene, —$(CH_2)_n$— where n is an integer from 1 to 5, —$C(R)H$— and —$C(R)HCH_2$—, where R is methyl or ethyl, and $b_4$) from 0 to 5 mol %, per mol of component b1), of a compound D having at least three groups capable of ester formation, the molar ratio of b1) to $b_2$) being from 0.4:1 to 1.5:1.

3. A biodegradable polyester Q1 having
a molecular weight ($M_n$) of from 5000 to 100,000 g/mol (measured by gel permeation chromatography),
a viscosity number of from 30 to 450 g/ml (measured in 50:50 by weight of o-dichlorobenzene/phenol at a concentration of 0.5% by weight of polyester Q1 at 25° C.), and
a melting point of from 50 to 235° C.,
and having both hydroxyl and carboxyl end groups, the molar ratio of carboxyl end groups to hydroxyl end groups being greater than one,
which is obtained by reacting a mixture consisting essentially of
$c_1$) a polyester P1 having
a molecular weight ($M_n$) of from 5000 to 50,000 g/mol (measured by gel permeation chromatography),
a viscosity number of from 30 to 350 g/ml (measured in a 50:50 by weight of o-dichlorobenzene/phenol at a concentration of 0.5% by weight of polyester P1 at 25° C.), and
a melting point of from 50 to 170° C.,
and having both hydroxyl and carboxyl end groups, the molar ratio of carboxyl end groups to hydroxyl end groups being greater than one,
and P1 being obtained by reacting a mixture consisting essentially of
$a_1$) a mixture consisting essentially of
from 45 to 80 mol % of adipic acid or ester-forming derivatives thereof, or mixtures thereof,
from 20 to 55 mol % of terephthalic acid or ester-forming derivatives thereof, or mixtures thereof, and
from 0 to 5 mol % of a sulfonate compound,
where the sum of the individual mol % percentages is 100 mol %, and
$a_2$) a dihydroxy compound selected from the group consisting of $C_2$–$C_6$-alkanediols and $C_5$–$C_{10}$-cycloalkanediols,
in the presence of from 0.01 to 5 mol %, per mol of component $a_1$), of a compound D having at least three groups capable of ester formation, the molar ratio of $a_1$) to $a_2$) being from 0.4:1 to 1.5:1,
or a polyester PWD, having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester PWD at 25° C.), and
a melting point of from 50 to 170° C.,
and having both hydroxyl and carboxyl end groups, the molar ratio of carboxyl end groups to hydroxyl end groups being greater than one,
and PWD being obtained by reacting essentially a component $a_1$) and a component $a_2$), the molar ratio of a ,) to $a_2$) being from 0.4:1 to 1.5:1,
or a mixture of P1 and PWD,
$c_2$) from 0.01 to 50% by weight, per weight of $c_1$), of a hydroxycarboxylic acid B1 being defined by the formula I$a$ or I$b$

  (Ia)

  (Ib)

where p is an integer from 1 to 1500, r is an integer from 1 to 4, and G is a radical selected from the group consisting of phenylene, —$(CH_2)_n$— where n is an integer from 1 to 5, —$C(R)H$— and —$C(R)HCH_2$—, where R is methyl or ethyl, and $c_3$) from 0 to 5 mol %, per mol of component $a_1$) of a compound D.

4. A biodegradable polyester Q2 having
a molecular weight ($M_n$) of from 6000 to 60,000 g/mol (measured by gel permeation chromatography),
a viscosity number of from 30 to 340 g/ml (measured in 50:50% by weight of o-dichlorobenzene/phenol at a concentration of 0.5% by weight of polyester Q2 at 25° C.), and
a melting point of from 50 to 170° C.,
which is obtained by reacting a mixture consisting essentially of
$d_1$) from 95 to 99.9% by weight of polyester P1 having
a molecular weight ($M_n$) of from 5000 to 50,000 g/mol (measured by gel permeation chromatography),
a viscosity number of from 30 to 350 g/ml (measured in a 50:50 by weight of o-dichlorobenzene/phenol at a concentration of 0.5% by weight of polyester P1 at 25° C.), and
a melting point of from 50° to 170° C.,
and having both hydroxyl and carboxyl end groups, the molar ratio of carboxyl end groups to hydroxyl end groups being greater than one,
and P1 being obtained by reacting a mixture consisting essentially of
$a_1$) a mixture consisting essentially of
from 45 to 80 mol % of adipic acid or ester forming derivatives thereof, or mixtures thereof,
from 20 to 55 mol % of terephthalic acid or ester-forming derivatives thereof, or mixtures thereof and
from 0 to 5 mol % of a sulfonate compound,
where the sum of the individual mol % percentages is 100 mol %, and
$a_2$) a dihydroxy compound selected from the group consisting of $C_2$–$C_6$-alkanediols and $C_5$–$C_{10}$-cycloalkanediols,
in the presence of from 0.01 to 5 mol %, per mol of component $a_1$), of a compound D having at least three groups capable of ester formation, the molar ratio of $a_1$) to $a_2$) being from 0.4:1 to 1.5:1,
or a polyester PWD, having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester PWD at 25° C.), and a melting point of from 50 to 170° C.,
and having both hydroxyl and carboxyl end groups, the molar ratio of carboxyl end groups to hydroxyl end groups being greater than one,
and PWD being obtained by reacting essentially a component $a_1$) and a component $a_2$), the molar ratio of a ,) to $a_2$) being from 0.4:1 to 1.5:1,
or a mixture of P1 and PWD, $d_2$) from 0.1 to 5% by weight of a bisoxazoline C1, $d_3$) from 0 to 5 mol %, per mol of component a ,), of a compound D, wherein the sum of the individual mol % percentages of $d_1$) and $d_2$) is 100 mol %.

5. A biodegradable polymer $T_1$ having a molecular weight ($M_n$) of from 10,000 to 100,000 g/mol (measured by gel permeation chromatography), a viscosity number of from 30 to 450 g/ml (measured in 50:50 by weight of o-dichlorobenzene/phenol at a concentration of 0.5% by weight of polymer $T_1$ at 25° C.), and a melting point of from 50 to 235° C., which is obtained by reacting the polyester Q1 having a molecular weight ($M_n$) of from 5000 to 100,000 g/mol (measured by gel permeation chromatography), a viscosity number of from 30 to 450 g/ml (measured in 50:50 by weight of o-dichlorobenzene/phenol at a concentration of 0.5% by weight of polyester Q1 at 25° C.), and a melting point of from 50 to 235° C., and having both hydroxyl and carboxyl end groups, the molar ratio of carboxyl end groups to hydroxyl end groups being greater than one, and Q1 being obtained by reacting a mixture consisting essentially of $c_1$) a polyester P1 having a molecular weight ($M_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester P1 at 25° C.), and a melting point of from 50 to 170° C., and having both hydroxyl and carboxyl end groups, the molar ratio of carboxyl end groups to hydroxyl end groups being greater than one, and P1 being obtained by reacting a mixture consisting essentially of $a_1$) a mixture consisting essentially of from 45 to 80 mol % of adipic acid or ester forming derivatives thereof, or mixtures thereof, from 20 to 55 mol % of terephthalic acid or ester-forming derivatives thereof, or mixtures thereof, and from 0 to 5 mol % of a sulfonate compound, where the sum of the individual mol % percentages is 100 mol %, and $a_2$) a dihydroxy compound selected from the group consisting of $C_2$–$C_6$-alkanediols and $C_5$–$C_{10}$-cycloalkanediols, in the presence of from 0.01 to 5 mol %, per mol of component $a_1$), of a compound D having at least three groups capable of ester formation, the molar ratio of $a_1$) to $a_2$) being from 0.4:1 to 1.5:1, or a polyester PWD having a molecular weight ($M_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester PWD at 25° C.), and a melting point of from 50 to 170° C., and having both hydroxyl and carboxyl end groups, the molar ratio of carboxyl end groups to hydroxyl end groups being greater than one, and PWD being obtained by reacting essentially a component $a_1$) and a component a2), the molar ratio of $a_1$) to $a_2$) being from 0.4:1 to 1.5:1, or a mixture of P1 and PWD, $c_2$) from 0.01 to 50% by weight, per weight of $c_1$), of a hydroxycarboxylic acid B3 being defined by the formula I$a$ or I$b$

(I$a$)

(I$b$)

where p is an integer from 1 to 1500, r is an integer from 1 to 4, and G is a radical selected from the group consisting of phenylene, —$(CH_2)_n$—where n is an integer from 1 to 5, —C(R)H— and —C(R)HCH$_2$—, where R is methyl or ethyl, and $c_3$) from 0 to 5 mol %, per mol of component $a_1$), of a compound D, with $e_1$) from 0.1 to 5% by weight, per mol of the polyester Q1, of bisoxazoline C1, and $e_2$) from 0 to 5 mol %, per mol of component $a_1$), of a compound D.

6. A biodegradable polymer T2 having a molecular weight ($M_n$) of from 10,000 to 100,000 g/mol (measured by gel permeation chromatography), a viscosity number of from 30 to 450 g/ml (measured in 50:50 by weight of o-dichlorobenzene/phenol at a concentration of 0.5% by weight of polymer T2 at 25° C.), and a melting point of from 50° to 235° C., which is obtained by reacting the polyester Q2 having a molecular weight ($M_n$) of from 6000 to 60,000 g/mol (measured by gel permeation chromatography), a viscosity number of from 30 to 340 g/ml (measured in 50:50% by weight of o-dichlorobenzene/phenol at a concentration of 0.5% by weight of polyester Q2 at 25° C.), and a melting point of from 50° to 170° C., and Q2 being obtained by reacting a mixture consisting essentially of $d_1$) from 95 to 99.9% by weight of polyester P1 a molecular weight ($M_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester P1 at 25° C.), and a melting point of from 50° to 170° C., and having both hydroxyl and carboxyl end groups, the molar ratio of carboxyl end groups to hydroxyl end groups being greater than one, and P1 being obtained by reacting a mixture consisting essentially of $a_1$) a mixture consisting essentially of from 45 to 80 mol % of adipic acid or ester-forming derivatives thereof, or mixtures thereof, from 20 to 55 mol % of terephthalic acid or ester-forming derivatives thereof, or mixtures thereof, and
from 0 to 5 mol % of a sulfonate compound,
where the sum of the individual mol % percentages is 100 mol %, and
a₂) a dihydroxy compound selected from the group consisting of $C_2$–$C_6$-alkanediols and $C_5$–$C_{10}$-cycloalkanediols,
in the presence of from 0.01 to 5 mol %, per mol of component a₁), of a compound D having at least three groups capable of ester formation, the molar ratio of a₁) to a₂) being from 0.4:1 to 1.5:1,
or a polyester PWD having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester PWD at 25° C), and
a melting point of from 50 to 170° C.,
and having both hydroxyl and carboxyl end groups, the molar ratio of carboxyl end groups to hydroxyl end groups being greater than one,
and PWD being obtained by reacting essentially a component a₁) and a component a₂), the molar ration of a₁) to a₂) being from 0.4:1 to 1.5:1,
or a mixture of P1 and PWD,
d₂) from 0.1 to 5% by weight of a bisoxazoline C1, and
d₃) from 0 to 5 mol %, per mol of component a ,), of a compound D,
where the sum of the individual mol % percentages of d1) and d₂) is 100 mol %, with
f1) from 0.01 to 50% by weight, per mol of polyester Q2, of hydroxycarboxylic acid B1 being defined by the formula I*a* or I*b*

 (Ia)

 (Ib)

where p is an integer from 1 to 1500, r is an integer from 1 to 4, and G is a radical selected from the group consisting of phenylene, —(CH2)$_n$—, where n is an integer from 1 to 5, —C(R)H— and —C(R)HCH₂—, where R is methyl or ethyl, and
f₂) from 0 to 5 mol %, per weight of component a₁), of a compound D.

7. A biodegradable polymer T3 having
a molecular weight ($M_n$) of from 10,000 to 100,000 g/mol (measured by gel permeation chromatography),
a viscosity number of from 30 to 450 g/ml (measured in 50:50 by weight of o-dichlorobenzene/phenol at a concentration of 0.5% by weight of polymer T3 at 25° C.), and
a melting point of from 50 ° to 235° C.,
which is obtained by reacting
g₁) a polyester P2, having
a molecular weight (M ,) of from 5000 to 80,000 g/mol (measured by gel permeation chromatography),
a viscosity number of from 30 to 450 g/ml (measured in 50:50 by weight of o-dichlorobenzene/phenol at a concentration of 0.5% by weight of polyester P2 at 25° C.), and
a melting point of from 50° to 235° C., and having both hydroxyl and carboxyl end groups, the molar ratio of carboxyl end groups to hydroxyl end groups being greater than one, and P2 being obtained by reacting a mixture consisting essentially of
b1) a mixture consisting essentially of
from 25 to 80 mol % of adipic acid or ester forming derivatives thereof, or mixtures thereof,
from 20 to 75 mol % of terephthalic acid or ester-forming derivatives thereof, or mixtures thereof, and
where the sum of the individual mol % percentages is 100 mol %, and
from 0 to 5 mol % of a sulfonate compound,
b₂) a dihydroxy compound selected from the group consisting of $C_2$–$C_6$-alkanediols and $C_5$–$C_{10}$-cycloalkanediols,
b₃) from 0.01 to 100% by weight, per mol of component b1), of a hydroxycarboxylic acid B1 being defined by the formula I*a* or I*b*

 (Ia)

 (Ib)

where p is an integer from 1 to 1500, r is an integer from 1 to 4, and G is a radical selected from the group consisting of phenylene, —(CH2)$_n$—, where n is an integer from 1 to 5, —C(R)H— and —C(R)HCH₂—, where R is methyl or ethyl, and
b₄) from 0 to 5 mol %, per mol of component b1), of a compound D having at least three groups capable of ester formation,
the molar ratio of b₁) to b₂) being from 0.4:1 to 1.5:1, or
g₂) a mixture consisting essentially of a polyester P1 having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester P1 at 25° C.), and
a melting point of from 50° to 170° C.,
and having both hydroxyl and carboxyl end groups, the molar ratio of carboxyl end groups to hydroxyl end groups being greater than one, and P1 being obtained by reacting a mixture consisting essential of
a₁) a mixture consisting essentially of
from 45 to 80 mol % of adipic acid or ester-forming derivatives thereof, or mixtures thereof,
from 20 to 55 mol % of terephthalic acid or ester-forming derivatives thereof, or mixtures thereof, and
from 0 to 5 mol % of a sulfonate compound,
where the sum of the individual mol % percentages is 100 mol %, and
a compound a₂) in the presence of from 0.01 to 5 mol %, per mol of component a₁), of a compound D, the molar ratio of a₁) to a₂) being from 0.4:1 to 1.5:1, and from 0.01 to 50% by weight, per mol of polyester P1, of hydroxycarboxylic acid B1, or
g₃) a mixture consisting essentially of polyesters P1 which have mutually different compositions, with from 0.1 to 5% by weight, per weight of the amount of polyesters g₁), g₂, or g₃), of bisoxazoline C1, and from 0 to 5 mol %, per mol of the respective molar quantities of component a ,), of a compound D.

8. A biodegradable thermoplastic molding composition T4 obtained by mixing of $h_1$) from 99.5 to 0.5% by weight of polyester Q2 having
a molecular weight ($M_n$) of from 6000 to 60,000 g/mol (measured by gel permeation chromatography),
a viscosity number of from 30 to 340 g/ml (measured in 50:50% by weight of o-dichlorobenzene/phenol at a concentration of 0.5% by weight of polyester Q2 at 25° C.), and
a melting point of from 50° to 170° C., and Q2 being obtained by reacting a mixture consisting essentially of $d_1$) from 95 to 99.9% by weight of polyester P1 having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester P1 at 25° C.), and
a melting point of from 50° to 170° C., and having both hydroxyl and carboxyl end groups, the molar ratio of carboxyl end groups to hydroxyl end groups being greater than one,
and P1 being obtained by reacting a mixture consisting essentially of $a_1$) a mixture consisting essentially of
from 45 to 80 mol % of adipic acid or ester forming derivatives thereof, or mixtures thereof,
from 20 to 55 mol % of terephthalic acid or esterforming derivatives thereof, or mixtures thereof, and
from 0 to 5 mol % of a sulfonate compound,
where the sum of the individual mol % percentages is 100 mol %, and $a_2$) a dihydroxy compound selected from the group consisting of $C_2$–$C_6$-alkanediols and $C_5$–$C_{10}$-cycloalkanediols, in the presence of from 0.01 to 5 mol %, per mol of component $a_1$), of a compound D having at least three groups capable of ester formation,
the molar ratio of $a_1$) to $a_2$) being from 0.4:1 to 1.5:1,
or a polyester PWD having a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester PWD at 25° C.), and
a melting point of from 50° to 170° C., and having both hydroxyl and carboxyl end groups, the molar ratio of carboxyl end groups to hydroxyl end groups being greater than one,
and PWD being obtained by reacting essentially a component $a_1$) and a component $a_2$), the molar ratio of a ,) to $a_2$) being from 0.4:1 to 1.5:1,
or a mixture of P1 and PWD, $d_2$) from 0.1 to 5% by weight of a bisoxazoline C1,
$d_3$) from 0 to 5 mol %, per mol of component $a_1$), of a compound D,
where the sum of the individual mol % percentages of $d_1$) and $d_2$) is 100 mol %, with $h_2$) from 0.5 to 99.5% by weight of hydroxycarboxylic acid B3 being defined by the formula Ia or Ib

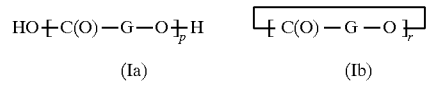

(Ia)          (Ib)

where p is an integer from 1 to 1500, r is an integer from 1 to 4, and G is a radical selected from the group consisting of phenylene, —$(CH_2)_n$—, where n is an integer from 1 to 5, —C(R)H— and —C(R)HCH$_2$—, where R is methyl or ethyl.

9. A process for preparing a biodegradable polyester P1, which has
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester P1 at 25° C.), and
a melting point of from 50° to 170° C.,
which comprises reacting a mixture consisting essentially of $a_1$) a mixture consisting essentially of
from 35 to 95 mol % of adipic acid or ester-forming derivatives thereof, or mixtures thereof,
from 5 to 65 mol % of terephthalic acid or ester-forming derivatives thereof, or mixtures thereof, and
from 0 to 5 mol % of a sulfonate compound,
where the sum of the individual mol % percentages is 100 mol %, and $a_2$) a dihydroxy compound selected from the group consisting of $C_2$–$C_6$-alkanediols and $C_5$–$C_{10}$-cycloalkanediols,
in the presence of from 0.01 to 5 mol %, per mol of $a_1$), of a compound D having at least three groups capable of ester formation,
the molar ratio of $a_1$) to $a_2$) being from 0.4:1 to 1.5:1.

10. A process for preparing a biodegradable polyester P2, which has
a molecular weight ($M_n$) of from 5000 to 80,000 g/mol (measured by gel permeation chromatography),
a viscosity number of from 30 to 450 g/ml (measured in 50:50 by weight of o-dichlorobenzene/phenol at a concentration of 0.5% by weight of polyester P2 at 25° C.), and
a melting point of from 50° to 235° C.,
and having both hydroxyl and carboxyl end groups, which comprises reacting a mixture consisting essentially of $b_1$) a mixture consisting essentially of
from 20 to 95 mol % of adipic acid or ester-forming derivatives thereof, or mixtures thereof,
from 5 to 80 mol % of terephthalic acid or ester forming derivatives thereof, or mixtures thereof, and
from 0 to 5 mol % of a sulfonate compound,
where the sum of the individual mol % percentages is 100 mol %, $b_2$) a dihydroxy compound selected from the group consisting of $C_2$–$C_6$-alkanediols and $C_5$–$C_{10}$-cycloalkanediols, $b_3$) from 0.01 to 100% by weight, per weight of component $b_1$), of a hydroxycarboxylic acid B1 being defined by the formula Ia or Ib $$HO\!\!-\!\!\!\left[\!C(O)\!-\!G\!-\!O\!\right]_{\!p}\!\!\!H \qquad \left[\!C(O)\!-\!G\!-\!O\!\right]_{\!r}$$
(Ia)          (Ib)

where p is an integer from 1 to 1500, r is an integer from 1 to 4, and G is a radical selected from the group consisting of phenylene, —$(CH_2)_n$—, where n is an integer from 1 to 5, —$C(R)H$— and —$C(R)HCH_2$—, where R is methyl or ethyl, and $b_4$) from 0 to 5 mol %, per mol of component $b_1$), of a compound D having at least three groups capable of ester formation, the molar ratio of $b_1$) to $b_2$) being from 0.4:1 to 1.5:1.

11. A process for preparing a biodegradable polyester Q1, which has
    a molecular weight ($M_n$) of from 5000 to 100,000 g/mol (measured by gel permeation chromatography),
    a viscosity number of from 30 to 450 g/ml (measured in 50:50 by weight of o-dichlorobenzene/phenol at a concentration of 0.5% by weight of polyester Q1 at 25° C.), and
    a melting point of from 50° to 235° C.,
which comprises reacting a mixture consisting essentially of
    $c_1$) a polyester P1 having
        a molecular weight ($M_n$) of from 5000 to 50,000 g/mol (measured by gel permeation chromatography),
        a viscosity number of from 30 to 350 g/ml (measured in 50:50 by weight of o-dichlorobenzene/phenol at a concentration of 0.5% by weight of polyester P1 at 25° C.), and
        a melting point of from 50° to 170° C.,
and having both hydroxyl and carboxyl end groups, the molar ratio of carboxyl end groups to hydroxyl end groups being greater than one, and P1 being obtained by reacting a mixture consisting essentially of
    $a_1$) a mixture consisting essentially of
        from 45 to 80 mol % of adipic acid or ester-forming derivatives thereof, or mixtures thereof,
        from 20 to 55mol % of terephthalic acid or ester-forming derivatives thereof, or mixtures thereof, and
        from 0 to 5 mol % of a sulfonate compound,
where the sum of the individual mol % percentages is 100 mol %, and
    $a_2$) a dihydroxy compound selected from the group consisting of $C_2$–$C_6$-alkanediols and $C_5$–$C_{10}$-cycloalkanediols,
in the presence of from 0.01 to 5 mol %, per mol of component $a_1$), of a compound D having at least three groups capable of ester formation, the molar ratio of $a_1$) to $a_2$) being from 0.4:1 to 1.5:1,
or a polyester PWD, having
    a molecular weight ($M_n$) of from 5000 to 50,000 g/mol (measured by gel permeation chromatography),
    a viscosity number of from 30 to 350 g/ml (measured in 50:50 by weight of o-dichlorobenzene/phenol at a concentration of 0.5% by weight of polyester PWD at 25° C.), and
    a melting point of from 50° to 170° C.,
and PWD being obtained by reacting essentially a component $a_1$) and a component $a_2$), the molar ratio of $a_1$) to $a_2$) being from 0.4:1 to 1.5:1,
or a mixture of P1 and PWD, $c_2$) from 0.01 to 50% by weight, per weight of $c_1$), of hydroxycarboxylic acid B1, being defined by the formula I*a* or I*b*

$$HO\!\!-\!\!\!\left[\!C(O)\!-\!G\!-\!O\!\right]_{\!p}\!\!\!H \qquad \left[\!C(O)\!-\!G\!-\!O\!\right]_{\!r}$$
(Ia)          (Ib)

where p is an integer from 1 to 1500, r is an integer from 1 to 4, and G is a radical selected from the group consisting of phenylene, —$(CH_2)_n$—, where n is an integer from 1 to 5, —$C(R)H$—and —$C(R)HCH_2$—, where R is methyl or ethyl, and $c_3$) from 0 to 5 mol %, per mol of component $a_1$), of a compound D.

12. A process for preparing a biodegradable polyester Q2, which has
    a molecular weight ($M_n$) of from 6000 to 60,000 g/mol (measured by gel permeation chromatography),
    a viscosity number of from 30 to 340 g/ml (measured in 50:50% by weight of o-dichlorobenzene/phenol at a concentration of 0.5% by weight of polyester Q2 at 25° C), and
    a melting point of from 50° to 170° C.,
which comprises reacting a mixture consisting essentially of
    $d_1$) from 95 to 99.9% by weight of polyester P1 having
        a molecular weight ($M_n$) of from 5000 to 50,000 g/mol (mea- sured by gel permeation chromatography),
        a viscosity number of from 30 to 350 g/ml (measured in 50:50 by weight of o-dichlorobenzene/phenol at a concentration of 0.5% by weight of polyester P1 at 25° C.), and
        a melting point of from 50° to 170° C.,
and having both hydroxyl and carboxyl end groups, the molar ratio of carboxyl end groups to hydroxyl end groups being greater than one,
and P1 being obtained by reacting a mixture consisting essentially of
    $a_1$) a mixture consisting essentially of
        from 45 to 80 mol % of adipic acid or ester-forming derivatives thereof, or mixtures thereof,
        from 20 to 55 mol % of terephthalic acid or ester-forming derivatives thereof, or mixtures thereof, and
        from 0 to 5 mol % of a sulfonate compound,
where the sum of the individual mol % percentages is 100 mol %, and
    $a_2$) a dihydroxy compound selected from the group consisting of $C_2$–$C_6$-alkanediols and $C_5$–$C_{10}$-cycloalkanediols,
in the presence of from 0.01 to 5 mol %, per mol of component $a_1$), of a compound D having at least three groups capable of ester formation,
the molar ratio of $a_1$) to $a_2$) being from 0.4:1 to 1.5:1, or a polyester PWD, having
    a molecular weight ($M_n$) of from 5000 to 50,000 g/mol (measured by gel permeation chromatography),
    a viscosity number of from 30 to 350 g/ml (measured in 50:50 by weight of o-dichlorobenzene/phenol at a concentration of 0.5% by weight of polyester PWD at 25° C.), and
    a melting point of from 50 to 170° C.,
and having both hydroxyl and carboxyl end groups, the molar ratio of carboxyl end groups to hydroxyl end groups being greater than one,
and PWD being obtained by reacting essentially a component $a_1$) and a component $a_2$), the molar ratio of $a_1$) to $a_2$) being from 0.4:1 to 1.5:1, or a mixture of P1 and PWD,
- $d_2$) from 0.1 to 5% by weight of a bisoxazoline C1, and
- $d_3$) from 0 to 5 mol %, per mol of component $a_1$), of a compound D.

13. A process for preparing a biodegradable polymer T1, which has
- a molecular weight ($M_n$) of from 10,000 to 100,000 g/mol (measured by gel permeation chromatography),
- a viscosity number of from 30 to 450 g/ml (measured in 50:50 by weight of o-dichlorobenzene/phenol at a concentration of 0.5% by weight of polymer T1 at 25° C.), and
- a melting point of from 50° to 235° C., which comprises reacting polyester Q1 having
  - a molecular weight ($M_n$) of from 5000 to 100,000 g/mol (measured by gel permeation chromatography),
  - a viscosity number of from 30 to 450 g/ml (measured in 50:50 by weight of o-dichlorobenzene/phenol at a concentration of 0.5% by weight of polyester Q1 at 25° C), and
  - a melting point of from 50° to 235° C., and having both hydroxyl and carboxyl end groups, the molar ratio of carboxyl end groups to hydroxyl end groups being greater than one,
and Q1 being obtained by reacting a mixture consisting essentially of $c_1$) a polyester P1 having
- a molecular weight ($M_n$) of from 5000 to 50,000 g/mol (measured by gel permeation chromatography),
- a viscosity number of from 30 to 350 g/ml (measured in 50:50 by weight of o-dichlorobenzene/phenol at a concentration of 0.5% by weight of polyester P1 at 25° C.), and
- a melting point of from 50° to 170° C., and having both hydroxyl and carboxyl end groups, the molar ratio of carboxyl end groups to hydroxyl end groups being greater than one,
and P1 being obtained by reacting a mixture consisting essentially of $a_1$) a mixture consisting essentially of
- from 45 to 80 mol % of adipic acid or ester-forming derivatives thereof, or mixtures thereof,
- from 20 to 55 mol % of terephthalic acid or ester-forming derivatives thereof, or mixtures thereof and
- from 0 to 5 mol % of a sulfonate compound, where the sum of the individual mol % percentages is 100% mol %, and
- $a_2$) a dihydroxy compound selected from the group consisting of $C_2$–$C_5$-alkanediols and the $C_5$–$C_{10}$-cycloalkanediols, in the presence of from 0.01 to 5 mol %, per mol of component $a_1$), of a compound D having at least three groups capable of ester formation, the molar ratio of $a_1$) to $a_2$) being from 0.4:1 to 1.5:1,
or a polyester PWD having
- a molecular weight ($M_n$) of from 5000 to 50,000 g/mol (measured by gel permeation chromatography),
- a viscosity number of from 30 to 350 g/ml (measured in 50:50 by weight of o-dichlorobenzene/phenol at a concentration of 0.5% by weight of polyester PWD at 25° C.), and
- a melting point of from 50° to 170° C., and having both hydroxyl and carboxyl end groups, the molar ratio of carboxyl end groups to hydroxyl end groups being greater than one,
and PWD being obtained by reacting essentially a component $a_1$) and a component $a_2$), the molar ratio of $a_1$) to $a_2$) being from 0.4:1 to 1.5:1, or a mixture of P1 and PWD,
- $c_2$) from 0.01 to 50% by weight, per weight of $c_1$), of hydroxycarboxylic acid B1, being defined by the formula I$a$ or I$b$ $$HO\text{-}[C(O)\text{-}G\text{-}O]_p\text{-}H \qquad [\text{-}C(O)\text{-}G\text{-}O\text{-}]_r$$
$$\text{(I}a\text{)} \qquad\qquad \text{(I}b\text{)}$$

where p is an integer from 1 to 1500, r is an integer from 1 to 4, and G is a radical selected from the group consisting of phenylene, —$(CH_2)_n$—, where n is an integer from 1 to 5, —C(R)H— and —C(R)HCH$_2$—, where R is methyl or ethyl, and

- $c_3$) from 0 to 5 mol %, per mol of component $a_1$), of a compound D, with
- $e_1$) from 0.1 to 5% by weight, per mol of the polyester Q1, of bisoxazoline C1, and
- $e_2$) from 0 to 5 mol %, per mol of component $a_1$), of a compound D.

14. A process for preparing a biodegradable polymer T2, which has
- a molecular weight ($M_n$) of from 10,000 to 100,000 g/mol (measured by gel permeation chromatography),
- a viscosity number of from 30 to 450 g/ml (measured in 50:50 by weight of o-dichlorobenzene/phenol at a concentration of 0.5% by weight of polymer T2 at 25° C.), and
- a melting point of from 50° to 235° C., which comprises reacting polyester Q2 having
- a molecular weight ($M_n$) of from 6000 to 60,000 g/mol (measured by gel permeation chromatography),
- a viscosity number of from 30 to 340 g/ml (measured in 50:50% by weight of o-dichlorobenzene/phenol at a concentration of 0.5% by weight of polyester Q2 at 25° C.), and
- a melting point of from 50° to 170° C., and Q2 being obtained by reacting a mixture consisting essentially of $d_1$) from 95 to 99.9% by weight of a polyester P1 having
- a molecular weight ($M_n$) of from 5000 to 50,000 g/mol (measured by gel permeation chromatography),
- a viscosity number of from 30 to 350 g/ml (measured in 50:50 by weight of o-dichlorobenzene/phenol at a concentration of 0.5% by weight of polyester P1 at 25° C.), and
- a melting point of from 50 to 170° C., and having both hydroxyl and carboxyl end groups, the molar ratio of carboxyl end groups to hydroxyl end groups being greater than one,
and P1 being obtained by reacting a mixture consisting essentially of where p is an integer from 1 to 1500, r is an integer from 1 to 4, and G is a radical selected from the group consisting of phenylene, —$(CH_2)_n$—, where n is an integer from 1 to 5, —C(R)H— and —C(R)HCH$_2$—, where R is methyl or ethyl,
and
- $f_2$) from 0 to 5 mol %, per mol of component $a_1$), of a compound D.

15. A process for preparing a biodegradable polymer T3, which has
- a molecular weight ($M_n$) of from 10,000 to 100,000 g/mol (measured by gel permeation chromatography), a viscosity number of from 30 to 450 g/ml (measured in 50:50 by weight of o-dichlorobenzene/phenol at a concentration of 0.5% by weight of polymer T3 at 25° C.), and a melting point of from 50° to 235° C., which comprises reacting g$_1$) polyester P2, having a molecular weight (M$_n$) of from 5000 to 80,000 g/mol (measured by gel permeation chromatography), a viscosity number of from 30 to 450 g/ml (measured in 50:50 by weight of o-dichlorobenzene/phenol at a concentration of 0.5% by weight of polyester P2 at 25° C), and a melting point of from 50° to 235° C., and having both hydroxyl and carboxyl end groups, the molar ratio of carboxyl end groups to hydroxyl end groups being greater than one, and P2 being obtained by reacting a mixture consisting essentially of b$_1$) a mixture consisting essentially of from 25 to 80 mol % of adipic acid or ester-forming derivatives thereof, or mixtures thereof, from 20 to 75% of terephthalic acid or ester-forming derivatives thereof, or mixtures thereof, and from 0 to 5 mol % of a sulfonate compound, where the sum of the individual mol % percentages is 100 mol %, and b$_2$) a dihydroxy compound selected from the group consisting of $C_2$-$C_6$-alkanediols and $C_5$-$C_{10}$-cycloalkanediols, b$_3$) from 0.01 to 100% by weight, per weight of component b$_1$), of a hydroxycarboxylic acid B1 being defined by the formula I$a$ or I$b$ a$_1$) a mixture consisting essentially of from 45 to 80 mol % of adipic acid or ester-forming derivatives thereof, or mixtures thereof, from 20 to 55% of terephthalic acid or ester-forming derivatives thereof, or mixtures thereof, and from 0 to 5 mol % of a sulfonate compound, where the sum of the individual mol % percentages is 100 mol %, and a$_2$) a dihydroxy compound selected from the group consisting of $C_2$-$C_6$-alkanediols and $C_5$-$C_{10}$-cycloalkanediols in the presence of from 0.01 to 5 mol %, per mol of component a$_1$), of a compound D having at least three groups capable of ester formation, the molar ratio of a$_1$) to a$_2$) being 0.4:1 to 1.5:1, or a polyester PWD having a molecular weight (M$_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester PWD at 25° C.), and a melting point of from 50° to 170° C., and having both hydroxyl and carboxyl end groups, the molar ratio of carboxyl end groups to hydroxyl end groups being greater than one, and PWD being obtained by reacting essentially a component a$_1$) and a component a$_2$), the molar ratio of a$_1$) to a$_2$) being from 0.4:1 to 1.5:1, or a mixture of P1 and PWD, d$_2$) from 0.1 to 5% by weight of a bisoxazoline C1, d$_3$) from 0 to 5 mol %, per mol of component a$_1$), of a compound D, where the sum of the individual mol % percentages of d$_1$) and d$_2$) is 100 mol %, with f$_1$) from 0.01 to 50% by weight, per weight of polyester Q2, of a hydroxycarboxylic acid B1 being defined by the formula I$a$ or I$b$

(Ia) (Ib)

(Ia) (Ib)

where p is an integer from 1 to 1500, r is an integer from 1 to 4, and G is a radical selected from the group consisting of phenylene, —(CH$_2$)$_n$—, where n is an integer from 1 to 5, —C(R)H— and —C(R)HCH$_2$—, where R is methyl or ethyl, and b$_4$) from 0 to 5 mol %, per mol of component b$_1$), of a compound D, the molar ratio of b$_1$) to b$_2$) being from 0.4:1 to 1.5:1, or g$_2$) a mixture consisting essentially of a polyester P1 having a molecular weight (M$_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester P1 at 25° C.), and a melting point of from 50° to 170° C., and having both hydroxyl and carboxyl end groups, the molar ratio of carboxyl end groups to hydroxyl end groups being greater than one, and P1 being obtained by reacting a mixture consisting essentially of a$_1$) a mixture consisting essentially of from 45 to 80 mol % of adipic acid or ester-forming derivatives thereof, or mixtures thereof, from 20 to 55 mol % of terephthalic acid or ester-forming derivatives thereof, or mixtures thereof, and from 0 to 5 mol % of a sulfonate compound, where the sum of the individual mol % percentages is 100 mol %, and and a compound a$_2$), the molar ratio of a$_1$) to a$_2$) being from 0.4:1 to 1.5:1, and from 0.01 to 50% by weight, per weight of polyester P1, of hydroxycarboxylic acid B1 being defined by the formula I$a$ or I$b$

(Ia) (Ib)

where p is an integer from 1 to 1500, r is an integer from 1 to 4, and G is a radical selected from the group consisting of phenylene, —(CH$_2$)$_n$—, where n is an integer from 1 to 5, —C(R)H— and —C(R)HCH$_2$—, where R is methyl or ethyl, or g$_3$) a mixture consisting essentially of polyesters P1 which have mutually different compositions, with from 0.1 to 5% by weight, per mol of the amount of polyesters, of bisoxazoline C1, and from 0 to 5 mol %, per mol of component a$_1$), of a compound D.

16. A process for preparing a biodegradable thermoplastic molding composition T4, which comprises mixing from 99.5 to 0.5% by weight of polyester Q2 having a molecular weight ($M_n$) of from 6000 to 60,000 g/mol (measured by gel permeation chromatography), a viscosity number of from 30 to 340 g/ml (measured in 50:50% by weight of o-dichlorobenzene/phenol at a concentration of 0.5% by weight of polyester Q2 at 25° C.), and a melting point of from 50° to 170° C., and Q2 being obtained by reacting a mixture consisting essentially of $d_1$) from 95 to 99.9% by weight of a polyester P1 having
a molecular weight ($M_n$) of from 5000 to 50,000 g/mol (measured by gel permeation chromatography),
a viscosity number of from 30 to 350 g/ml (measured in 50:50 by weight of o-dichlorobenzene/phenol at a concentration of 0.5% by weight of polyester P1 at 25° C.), and
a melting point of from 50° to 170° C., and having both hydroxyl and carboxyl end groups, the molar ratio of carboxyl end groups to hydroxyl end groups being greater than one, and P1 being obtained by reacting a mixture consisting essentially of $a_1$) a mixture consisting essentially of
from 45 to 80 mol % of adipic acid or ester forming derivatives thereof, or mixtures thereof,
from 20 to 55 mol % of terephthalic acid or ester-forming derivatives thereof, or mixtures thereof, and
from 0 to 5 mol % of a sulfonate compound,
where the sum of the individual mol % percentages is 100 mol %, and $a_2$) a dihydroxy compound selected from the group consisting of $C_2$–$C_5$-alkanediols and $C_5$–$C_{10}$-cycloalkanediols, in the presence of from 0.01 to 5 mol %, per mol of component $a_1$), of a compound D having at least three groups capable of ester formation, the molar ratio of $a_1$) to $a_2$) being from 0.4:1 to 1.5:1, or a polyester PWD having a molecular weight ($M_n$) of from 5000 to 50,000 g/mol (measured by gel permeation chromatography), a viscosity number of from 30 to 350 g/ml (measured in 50:50 by weight of o-dichlorobenzene/phenol at a concentration of 0.5% by weight of polyester PWD at 25° C.), and a melting point of from 50° to 170° C., and having both hydroxyl and carboxyl end groups, the molar ratio of carboxyl end groups to hydroxyl end groups being greater than one, and PWD being obtained by reacting essentially a component $a_1$) and a component $a_2$), the molar ratio of $a_1$) to $a_2$) being from 0.4:1 to 1.5:1, or a mixture of P1 and PWD, $d_2$) from 0.1 to 5% by weight of a bisoxazoline C1, $d_3$) from 0 to 5 mol %, per mol of component $a_1$), of a compound D, where the sum of the individual mol % percentages of $d_1$) and $d_2$) is 100 mol %, with from 0.5 to 99.9% by weight of hydroxycarboxylic acid B1 being defined by the formula I$a$ or I$b$

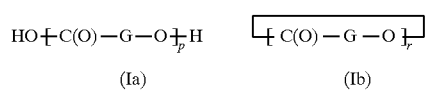

where p is an integer from 1 to 1500, r is an integer from 1 to 4, and G is a radical selected from the group consisting of phenylene, —$(CH_2)_n$—, where n is an integer from 1 to 5, —C(R)H— and —C(R)HCH$_2$—, where R is methyl or ethyl.

17. A compostable molding comprising the biodegradable polyester P1 defined in claim 1.

18. An adhesive comprising the biodegradable polyester P1 defined in claim 1.

19. A biodegradable blend comprising the biodegradable polyester P1 defined in claim 1 and starch.

20. A biodegradable foam comprising the biodegradable polyester P1 defined in claim 1.

21. A paper coating composition comprising the biodegradable polyester P1 defined in claim 1.

* * * * *

UNITED STATES PATENT AND TRADEMARK OFFICE
CERTIFICATE OF CORRECTION

PATENT NO. : 5,889,135  
DATED : March 30, 1999  
INVENTOR(S) : WARZELHAN, ET AL Page 1 of 3

It is certified that error appears in the above-identified patent and that said Letters Patent is hereby corrected as shown below:

Delete "mol % percentages" and substitute --mole percentages-- in the following places:
  col. 16, claim 1, lines 27 and Col. 16, claim 2, lines 56;
  col. 17, claim 3, line 48;
  col. 18, claim 4, line 52;
  col. 19, claim 4, line 12 and claim 5, line 56;
  col. 21, claim 6, lines 4 and 32;
  col. 22, claim 7, lines 10 and 55;
  col. 23, claim 8, line 35;
  col. 24, claim 9, line 30 and claim 10, line 59;
  col. 25, claim 11, line 45;
  col. 26, claim 12, line 44;
  col. 27, claim 13, line 45;
  col. 29, claim 15, lines 26 and 40; and
  col. 30, claim 15, lines 1 and 43.

Delete "a ,)" and substitute --$a_1$)-- in the following places:
  col. 18, claim 3, line 2;
  col. 19, claim 4, lines 6 and 10;
  col. 21, claim 6, line 30;
  col. 22, claim 7, line 67; and
  col. 23, claim 8, line 57.

UNITED STATES PATENT AND TRADEMARK OFFICE
CERTIFICATE OF CORRECTION

PATENT NO. : 5,889,135
DATED : March 30, 1999
INVENTOR(S) : WARZELHAN, ET AL

It is certified that error appears in the above-identified patent and that said Letters Patent is hereby corrected as shown below:

Delete "B3" and substitute --B1-- in the following places:
    col. 20, claim 5, line 15; and
    col. 23, claim 8, line 67.

Delete "C.)." and substitute --C.),-- in the following places:
    col. 19, claim 5, lines 21, 29 and 43; and
    col. 31, claim 16, line 43.

Col. 26, claim 12, line 28, "(mea- sured" should be --(measured--.

Col. 20, claim 5, line 10, "a2)," should be --$a_2$),--.

Col. 22, claim 7, lines 5, 17 and 31, "b1)," should be --$b_1$),--.

UNITED STATES PATENT AND TRADEMARK OFFICE
CERTIFICATE OF CORRECTION

PATENT NO. : 5,889,135
DATED : March 30, 1999
INVENTOR(S) : WARZELHAN, ET AL

It is certified that error appears in the above-identified patent and that said Letters Patent is hereby corrected as shown below:

Delete "-CH2)$_n$-" and substitute -- -CH$_2$)$_n$- -- in the following places:
   col. 21, claim 6, line 45; and
   col. 22, claim 7, line 28.

On the cover page, item [22], the PCT filing date should be --Feb. 3, 1996--.

Signed and Sealed this

Seventeenth Day of August, 1999

Attest:

Q. TODD DICKINSON

*Attesting Officer*      *Acting Commissioner of Patents and Trademarks*